(12) United States Patent
Haensler

(10) Patent No.: US 7,767,658 B2
(45) Date of Patent: Aug. 3, 2010

(54) VACCINE COMPOSITION

(75) Inventor: Jean Haensler, Grezieu la Varenne (FR)

(73) Assignee: Aventis Pasteur SA, Lyons Cedex (FR)

( * ) Notice: Subject to any disclaimer, the term of this patent is extended or adjusted under 35 U.S.C. 154(b) by 372 days.

(21) Appl. No.: 11/971,751

(22) Filed: Jan. 9, 2008

(65) Prior Publication Data

US 2008/0131446 A1 Jun. 5, 2008

Related U.S. Application Data

(62) Division of application No. 10/989,154, filed on Nov. 15, 2004, now Pat. No. 7,344,720.

(60) Provisional application No. 60/611,925, filed on Sep. 22, 2004.

(30) Foreign Application Priority Data

Nov. 17, 2003 (FR) .................................. 03 13406

(51) Int. Cl.
A61K 30/00 (2006.01)
(52) U.S. Cl. ....................................................... 514/78
(58) Field of Classification Search .................... 514/78
See application file for complete search history.

(56) References Cited

FOREIGN PATENT DOCUMENTS

WO 02/26209 A2 4/2002

OTHER PUBLICATIONS

Jiao, X. et al., "Modulation of Cellular Immune Response Against Hepatitis C Virus Nonstructural Protein 3 by Cationic Liposome Encapsulated DNA Immunization", Hepatology, vol. 37, No. 2, Feb. 2003, 452-460.
Gorman, CM et al., "Efficient in Vivo Delivery of DNA to Pulmonary Cells Using the Novel Lipid EDMPC", Gene Therapy, vol. 4, No. 9, 1997, 983-992.
MacDonald, Robert C. et al., "Physical and Biological Properties of Cationic Triesters of Phosphatidylcholine", Biophysical Journal, vol. 77, No. 5, Nov. 1999, 2612-2629.
Rosenzweig, Howard S. et al., "O-Alkyl Dioleoylphosphatidylcholinium Compounds: The Effect of Varying Alkyl Chain Length on Their Physical Properties and In Vitro DNA Transfection Activity", Bioconjugate Chemistry, vol. 11, No. 3, May 2000, 306-313.

*Primary Examiner*—Rei-tsang Shiao
(74) *Attorney, Agent, or Firm*—McDonnell Boehnen Hulbert & Berghoff LLP

(57) ABSTRACT

The present invention relates to a pharmaceutical composition comprising at least one vaccine antigen, which also comprises at least one phosphoric ester derivative of phosphatidylcholine having the structure:

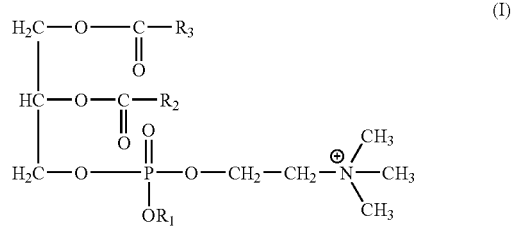

in which:
$R_1$ is a lower alkyl,
$R_2$ and $R_3$ are identical or different, and can each represent linear hydrocarbon-based chains having from 13 to 21 carbon atoms.

6 Claims, No Drawings

VACCINE COMPOSITION

This application is a division of U.S. patent application Ser. No. 10/989,154 filed on Nov. 15, 2004, which claims priority to U.S. Provisional Patent Application No. 60/611,925 filed on Sep. 22, 2004, the disclosure of which is incorporated herein by reference.

The present invention relates to the field of vaccines, and more particularly to adjuvanted vaccines. In particular, the invention relates to pharmaceutical compositions comprising at least one vaccine antigen and at least one phosphoric ester derivative of phosphatidylcholine.

According to the prior art, it is known practice to increase or orient the immune response induced by the antigens present in a vaccine by means of adjuvants. This may be desirable because the antigen, administered alone, is not sufficiently immunogenic, due in particular to its very high degree of purity, or because it is desired to decrease the amount of antigens present in the vaccine or the number of boosters to be given, or else because it is desired to prolong the duration of protection conferred by the vaccine. Sometimes, it is a question of qualitatively rather than quantitatively modifying the induced response.

Although in the prior art there is an abundance of proposed products which may be used as adjuvants, it is noted that most of the adjuvanted vaccines which are the subject of a marking authorization in human medicine are adjuvanted by means of an aluminum salt, or of an emulsion.

Now, there is a real demand for the availability of novel adjuvants whose qualities will make it possible to modify the immune response while at the same time conserving the qualities of a completely safe administration.

Moreover, in another field, which is that of transfection, the use of cationic lipids has been proposed in the state of the art. Thus, for example, in the publication entitled "*Modulation of Cellular Immune Response Against Hepatitis C Virus Nonstructural Protein 3 by Cationic Liposome Encapsulated DNA Immunization*", several cationic lipids constituting liposomes are tested for their ability to transport the plasmid DNA of interest to the cells. This publication is of value in the vaccines field since the transfected DNA encodes antigens against which an immune system response is desired. In order for there to be a good reaction of the immune system, it is first of all necessary for the antigen to be expressed, and therefore for the DNA to "delivered" under the best conditions to the cells capable of expressing it. The role played by the transfecting agents which act as a "transporter" for the DNA is different to the role played by an adjuvant which accompanies a vaccine antigen present in a pharmaceutical composition.

The results obtained by the authors of that publication show that the response obtained is greater when the DNA is transported by means of liposomes rather than when the DNA is injected "naked"; however, depending on the nature of the lipids used to form the liposomes, the responses obtained vary in nature and in intensity.

Despite the abundant literature on the various products which may be used as adjuvants, there is still a need for a product which can be used without any risk to the organism to which it is administered, and which makes it possible to increase and/or to modify the response of the immune system with respect to the vaccine antigen with which it is administered.

One of the aims of the invention is to provide such a product.

Another aim of the invention is to provide a readily available vaccine adjuvant, the cost of which is such that it may be added to vaccine compositions without increasing the cost price thereof in a prohibitive manner.

To achieve these aims, a subject of the present invention is a pharmaceutical composition comprising at least one vaccine antigen, which also comprises at least one phosphoric ester derivative of phosphatidylcholine having the structure:

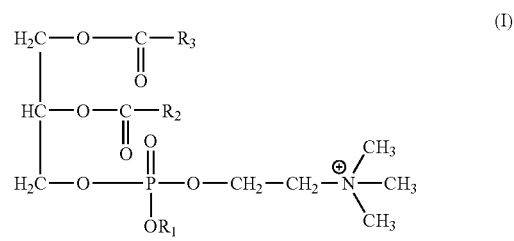

in which:

$R_1$ is a lower alkyl, $R_2$ and $R_3$ are identical or different, and can each represent linear hydrocarbon-based chains having from 13 to 21 carbon atoms.

According to a particular embodiment, $R_1$ represents the ethyl radical; thus, the degradation of this derivative in the organism to which it has been administered will produce biocompatible products: phosphatidylcholines and ethanol.

According to a particular embodiment of the invention, $R_2$ and $R_3$ are chosen from the radicals originating from the following fatty acids: myristic acid, palmitic acid, stearic acid and oleic acid.

According to a particularly advantageous embodiment, $R_2$ and $R_3$ are both identical and represent the oleic acid radical. Such a product which can be entirely prepared by chemical synthesis provides all the guarantees of safety and of reproducibility desired for pharmaceutical use.

A subject of the invention is also the use of a phosphoric ester derivative of phosphatidylcholine having the structure:

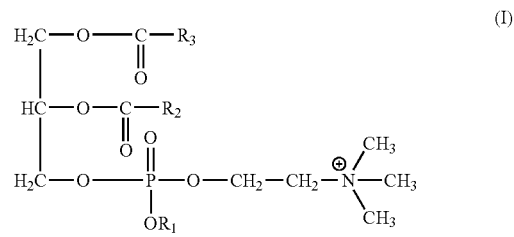

in which:

$R_1$ is a lower alkyl, $R_2$ and $R_3$ are identical or different, and can each represent linear hydrocarbon-based chains having from 13 to 21 carbon atoms, for preparing a vaccine adjuvant.

A subject of the invention is also a method for immunizing a mammal, according to which at least one vaccine antigen is administered to said mammal and also administered to said mammal is a phosphoric ester derivative of phosphatidylcholine having the structure:

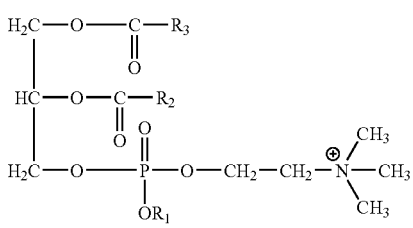

in which:
R$_1$ is a lower alkyl,
R$_2$ and R$_3$ are identical or different, and can each represent linear hydrocarbon-based chains having from 13 to 21 carbon atoms.

Thus, the response of the immune system is modified compared to the response which would be obtained if the vaccine antigen was administered without phosphatidylcholine derivative.

Many other advantages of the present invention will emerge on reading the detailed description which follows.

The present invention relates to a pharmaceutical composition comprising at least one vaccine antigen. The term "vaccine antigen" is intended to mean an antigen capable of inducing a response of the immune system when it is administered to humans or to an animal. This response of the immune system can result in a production of antibodies or in an activation of certain cells, in particular antigen-presenting cells (for example: dendritic cells), T lymphocytes, B lymphocytes.

The pharmaceutical composition may be a composition for prophylactic purposes or therapeutic purposes, or else both.

It may be administered via all the routes conventionally used or recommended for vaccines: parenteral route, mucosal route, and may be in various forms: injectable or sprayable liquid, formulation which has been freeze-dried or dried by atomization or air-dried, etc. It may be administered by means of a syringe or by means of a needle-free injector for intramuscular, subcutaneous or intradermal injection. It may also be administered by means of a nebulizer capable of delivering a dry powder or a liquid spray to the mucous membranes, whether they are nasal, pulmonary, vaginal or rectal.

The vaccine antigens used in the pharmaceutical compositions according to the present invention are "direct" antigens, i.e. they are not DNA encoding these antigens, but the antigens themselves; they may be a whole microorganism or only part of this microorganism; thus, among the antigens conventionally used in vaccines, mention may be made of:
polysaccharides, whether they are alone or conjugated to carrier elements, such as carrier proteins,
live attenuated whole microorganisms,
inactivated microorganisms,
recombinant peptides and proteins,
glycoproteins, glycolipids, lipopeptides,
synthetic peptides,
ruptured microorganisms in the case of vaccines referred to as "split" vaccines.

These antigens are antigens used or capable of being used for the treatment or prevention of various diseases, such as, for example: diphtheria, tetanus, polio, rabies, whooping cough, hepatitis A, B and C, yellow fever, typhoid fever, chicken pox, measles, mumps, German measles, Japanese encephalitis, meningitis, pneumococcal infections, rotavirus infections, AIDS, cancers, tuberculosis, Lyme disease, RSV infections, herpes, bacterial ailments caused by Chlamydia, Neisseria gonorrheae, Streptococcus pneumoniae, Moraxella catarrhalis, Staphylococcus aureus or Haemophilus influenza type B, malaria, leishmaniasis, listeriosis, etc.

The pharmaceutical composition according to the invention may be a composition intended for immunization against a single pathogen or cancer, i.e. it comprises one or more antigens of a single pathogen or cancer, or else it may be a composition intended for immunization against several pathogens or cancers (this is then referred to as a vaccine combination).

The action of the phosphoric ester derivative of phosphatidylcholine used is to adjuvant the vaccine composition, i.e. to increase or to modify the immune system response of the organism to which the vaccine composition is administered, compared to the response which would be obtained in the absence of such a compound. In particular, it may be an increase in the humoral response, or in the cellular response, or in both. The action may also be, not an increase in response, but a different orientation of the induced response: for example, an orientation toward a cellular response rather than a humoral response, production of certain cytokines rather than of others, production of certain types or subtypes of antibodies rather than of others, stimulation of certain cells rather than of others, etc. The action of the adjuvant may also consist in increasing the duration of the immune response over time. It may also involve making it possible to decrease the number of administrations required to obtain protection for the individual immunized, or else to decrease the amount of antigen contained in the administered dose.

The adjuvant action of the derivative according to the invention can be obtained either when it is combined with the antigen(s) of the pharmaceutical composition when they are administered, i.e. when it is present directly in the pharmaceutical composition, or else when it is administered separately from the antigen(s) whose immunogenic power it is desired to modify. However, it is preferred to use it in the same pharmaceutical composition as the antigen(s) to be administered. For the purposes of the present invention, the term "phosphatidylcholine" is intended to mean phospholipids consisting of a molecule of glycerol, of 2 fatty acids, of a phosphate group and of choline. These compounds, also referred to as lecithins, vary according to their fatty acids.

For the needs of the invention, the 2 fatty acids R$_2$ and R$_3$ may be identical or different, saturated or unsaturated; use is preferably made of phosphatidylcholines originating from the esterification of fatty acids having at least 13 carbon atoms, and in particular of the following acids: myristic acid, palmitic acid, stearic acid or oleic acid.

The term "lower alkyl radical R$_1$" is intended to mean an alkyl radical having at most 5 carbon atoms. Specifically, according to the invention, the phosphatidylcholine derivative is a phosphoric ester of a phosphatidylcholine; it may be an ester originating from the reaction of phosphatidylcholine and of methanol, ethanol, propanol, butanol or pentanol; particularly good results have been obtained with an ester originating from ethanol.

The compounds suitable for the purposes of the invention can be obtained by complete chemical synthesis or else by esterification of natural phosphatidylcholines, such as the phosphatidylcholine extracted from soybean or from eggs. These are compounds which can be used in the form of a pharmaceutically acceptable salt, in particular in chloride form. Among the compounds which are particularly suitable, mention may be made of 1,2-dilauroyl-sn-glycero-3-ethylphosphocholine, 1,2-dimyristoyl-sn-glycero-3-ethylphosphocholine, 1,2-dipalmitoyl-sn-glycero-3-ethylphosphocholine, 1,2-distearoyl-sn-glycero-3-ethylphosphocholine, 1,2-dioleoyl-sn-glycero-3-ethylphosphocholine or else 1,2-palmitoyloleoyl-sn-glycero-3-ethylphosphocholine, which are in particular available from the company Avanti® Polar Lipids Inc. These compounds are available in the form of a powder or in solution in chloroform.

According to the invention, the compounds are dispersed in water or in an aqueous buffer so as to form a suspension which is then mixed with a solution comprising the vaccine antigens, or else the suspension containing the phosphoric ester derivative of phosphatidylcholine is used to take up a lyophilizate comprising the vaccine antigens.

Alternatively, it is possible to disperse or to hydrate the ester derivative of phosphatidylcholine with water or a buffer already comprising at least one vaccine antigen.

The phosphoric ester derivatives of phosphatidylcholine used may then form lipid vesicles, or liposomes, the size of which is advantageously between 50 and 220 nm.

It is also possible to use the adjuvants according to the invention in a composition comprising an emulsion.

The following examples illustrate, in a nonlimiting manner, examples of implementation of the present invention.

EXAMPLE 1

Vaccine Compositions Having the TAT Protein as Antigen 1.1. Preparation of the Compositions Vaccine compositions are prepared comprising, as vaccine antigen, a recombinant protein which can be used in a vaccine against AIDS; it is the detoxified TAT III B protein, which is obtained by expression in *E. coli* and purification through various chromatography steps, then chemical inactivation, as is described in application WO99/33346, where it is identified under the term "carboxymethylated Tat".

The compositions are prepared in the manner described below.

Powdered 1,2-dioleoyl-sn-glycero-3-ethylphosphocholine (ethyl PC) chloride is provided, supplied by the company Avanti® Polar Lipids Inc., and is solubilized in a 4/1 chloroform/methanol mixture so as to obtain a concentration of 2 mg/mL.

3.18 mL of the solution obtained, i.e. 6.36 mg of ethyl PC, are introduced into a glass round-bottomed flask; the solvent is removed using a rotary evaporator until an even lipid film is obtained on the wall of the round-bottomed flask. This film is then dried under a strong vacuum so as to remove any trace of residual solvent.

The film is then rehydrated with 4 ml of distilled water at 40° C., using a sonication bath. The dispersion of vesicles thus obtained is extruded through several polycarbonate membranes (0.8 µm; 0.4 µm and 0.2 µm) mounted on an extruder (Lipex Biomembranes, Inc.) thermostated at 50° C. under nitrogen pressure.

The liposomal suspension then obtained, having a concentration of 1.59 mg/mL, is mixed volume for volume with the concentrated Tat solution at 200 µg/mL in buffer consisting of 100 mmol/L TRIS, 200 mmol/L NaCl, pH 7.4.

A composition comprising only the TAT antigen, without adjuvant, is also prepared. Doses of 200 µl are thus obtained, the compositions of which are as follows:
1) 20 µg of TAT
2) 20 µg of TAT and 159 µg of ethyl PC 1.2. Immunization.

2 groups of six 8-week-old female BALB/c mice are injected with one of the compositions prepared in paragraph 1.1, subcutaneously, at a rate of one dose of 200 µl per mouse; the injections are given on D0 and on D21.

Blood samples are taken from the retro-orbital sinus on D14 in order to assess the primary response and on D35 for the secondary response. The specific IgG1 and IgG2a titers are determined using standardized ELISA assays.

The mice are sacrificed on D37; their spleen is removed and the splenocytes are isolated.

The results obtained regarding the humoral responses are recapitulated in the table below, in which the IgG titers are expressed in arbitrary ELISA units (log10).

For each group of mice, the value indicated is the mean geometric titer of the values obtained for each of the mice.

| Groups of mice | IgG1 titer on D14 | IgG2a titer on D14 | IgG1 titer on D35 | IgG2a titer on D35 |
| --- | --- | --- | --- | --- |
| Tat alone | 1.943 | 1.045 | 3.950 | 2.437 |
| Tat + ethylPC | 2.931 | 2.429 | 4.889 | 4.368 |

The results obtained show that the compositions according to the invention make it possible to obtain a humoral response which is clearly greater than that obtained when the antigen is administered alone.

It is observed that the adjuvant effect is clearly evident with respect to the IgG2a response, which is an indication of an immune response oriented rather toward a TH1-type response.

To assess the effect of the pharmaceutical compositions according to the invention on the cellular response, counts of spleen cells capable of producing γ-interferon are performed using an ELISPOT assay. This assay is carried out both on fresh cells and on restimulated cells.

To carry out the assay, the spleen cells are cultured in cell culture plates, at a rate of 200 000 cells per well, in the presence either of medium alone, or of the recombinant TAT antigen. After culturing for 16 hours, the ELISPOT is developed, i.e. the number of spots corresponding to the cells secreting γ-interferon is counted. The results obtained are summarized in the tables below, the values indicated are the mean values (per group of mice) of the differences, calculated for each mouse, between the number of spots counted per million cells in the wells having recombinant TAT and the number of spots counted per million cells in the wells having only medium.

The table below summarizes the results obtained on fresh cells.

| Pharmaceutical composition tested | Number of spots per million cells |
| --- | --- |
| TAT at 20 µg | 31.67 |
| TAT at 20 µg + ethylPC | 129.17 |

The table below summarizes the results obtained on cells restimulated with recombinant TAT in the presence of IL2.

| Pharmaceutical composition tested | Number of spots per million cells |
| --- | --- |
| TAT at 20 µg | 44.16 |
| TAT at 20 µg + ethylPC | 411.66 |

These results show the positive effect obtained using a pharmaceutical composition according to the present invention, on the stimulation of CD4+ cells.

2. Vaccine Compositions having the Cytomegalovirus Glycoprotein gB as Antigen 2.1. Preparation of the Compositions Vaccine compositions comprising, as vaccine antigen, a recombinant protein derived from an envelope glycoprotein of the cytomegalovirus (CMV) Towne strain, called gB, the nucleotide and protein sequences of which are described in patent U.S. Pat. No. 5,834,307, are prepared. This recombinant protein is produced by a recombinant CHO line transfected with a plasmid called pPRgB27clv4, which contains a modified gB gene. In fact, in order to facilitate the production of this recombinant protein by the CHO line, the gB gene was modified beforehand by deleting the part of the gene which encodes the transmembrane region of the gB protein corresponding to the amino acid sequence between valine 677 and arginine 752 and by introducing 3 point mutations such that the existing cleavage site in the native gB was deleted. In fact, the recombinant protein produced by the recombinant CHO line corresponds to a truncated gB protein lacking a cleavage site and a transmembrane region, called gBdTM.

The construction of the plasmid pPRgB27clv4 and the production of the truncated gB protein (gBdTM) by the recombinant CHO line are described in U.S Pat. No. 6,100,064. The purification of the truncated gB protein is carried out on an immunoaffinity chromatographic column using the 15D8 monoclonal antibody described by L. Rasmussen et al. (J. Virol. (1985) 55: 274-280).

Powdered 1,2-distearoyl-sn-glycero-3-ethylphosphocholine (ethyl DSPC) chloride and 1,2-dioleoyl-sn-glycero-3-ethylphosphocholine (ethyl DOPC) chloride are provided, supplied by the company Avanti® Polar Lipids Inc. For each of the products, the following operations are carried out:

5 mg of powder are solubilized in 5 ml of 4:1 (vol/vol) chloroform/methanol. The solution is dried in a glass round-bottomed flask by means of a rotary evaporator so as to leave a lipid film over the walls of the round-bottomed flask. This film is then dried under a strong vacuum so as to remove all traces of residual solvent, and is then taken up in 2.5 ml of water at 60° C. for a final concentration of 2 mg/ml. The resulting liposomal suspension is homogenized by vortexing for 10 minutes, and sonication in an ultrasound bath for 5 minutes, and is then extruded, by means of a Lipex extruder (Northern Lipids Inc., Vancouver, CA) thermostated at 50° C., in five passages through a polycarbonate membrane with a porosity of 0.2 µm.

A formulation comprising ethyl PC in emulsion is also prepared.

For this, 25 mg of 1,2-dioleoyl-sn-glycero-3-ethylphosphocholine chloride (ethyl DOPC—Avanti Polar Lipids) are solubilized in a glass round-bottomed flask by means of 10 ml of 4:1 (vol/vol) chloroform/methanol. The solution obtained is dried by means of a rotary evaporator so as to leave a lipid film over the walls of the round-bottomed flask. This film is then dried under a strong vacuum so as to remove all traces of residual solvent.

375 mg of plant Tween® 80, provided by the company Merck, are weighed out into a beaker, and 29.29 g of water are added thereto and the mixture is stirred until the surfactant has completely dissolved.

The lipid film obtained in the preceding step is then taken up with this solution of Tween® 80. 1475 mg of squalene (Fluka) are added to this suspension and the emulsion obtained is homogenized with an Ultraturrax (8000-9500 rpm) and then with an M110 microfluidizer (Microfluidics, Newton, Mass.), 20 passages at 60 psi. The final concentration of squalene in this emulsion is 5%.

The immunization doses are prepared by mixing the adjuvant formulations described above, or water, with an aqueous stock solution of antigen at 160 µg/ml of gB protein and with PBS buffer, so as to obtain doses of 50 µl having the following compositions:
1) 2 µg of gB
2) 2 µg of gB and 50 µg of ethyl DOPC,
3) 2 µg of gB and 50 µg of ethyl DSPC,
4) 2 µg of gB, 50 µg of ethyl DOPC, 1.25 mg of squalene and 0.3 mg of Tween® 80.

2.2. Immunization 4 groups of eight 8-week-old female OF1 non-inbred mice are provided, and are injected with one of the compositions prepared in paragraph 2.1, subcutaneously, at a dose of 50 µl per mouse; the injections are given on D0 and on D21.

Blood samples are taken from the retroorbital sinus on D20 in order to assess the primary response, and on D34 for the secondary response. The specific IgG1 and IgG2a titers are determined by means of standard ELISA assays.

The mice are sacrificed on D37; their spleen is removed and the splenocytes are isolated and stimulated with recombinant gB protein, or not stimulated.

The concentration of cytokines (IL5, $\gamma$-IFN and TNF-$\alpha$) in the supernatants from spleen cells stimulated for 5 days with gB protein, and also in the supernatants from non-stimulated cells, is then determined by means of ELISA assays, in order to deduce therefrom, by comparison, the specific production of cytokines.

The results obtained with regard to the humoral responses are recapitulated in the table below, in which the IgG titers are expressed in arbitrary ELISA units (log10).

For each group of mice, the value indicated is the mean geometric titer of the values obtained for each of the mice.

| Groups of mice | IgG1 titer at D21 | IgG2a titer at D21 | IgG1 titer at D35 | IgG2a titer at D35 |
|---|---|---|---|---|
| gB alone | 2.703 ± 0.773 | 1.624 ± 0.572 | 4.409 ± 0.564 | 3.187 ± 0.595 |
| gB + ethyl DOPC | 3.673 ± 0.521 | 3.763 ± 0.371 | 4.472 ± 0.453 | 4.741 ± 0.260 |
| gB + ethyl DSPC | 3.708 ± 0.545 | 3.869 ± 0.303 | 4.388 ± 0.393 | 4.600 ± 0.246 |
| gB + ethyl DSPC + emulsion | 4.205 ± 0.388 | 2.944 ± 0.445 | 5.294 ± 0.416 | 4.272 ± 0.348 |

The results for the cytokines are given in the table below; the values indicated are, for each cytokine, the difference in pg/ml between the mean of the amounts of cytokines measured for the cells restimulated with gB protein, and the mean of the amounts of cytokines measured for the cells cultured in medium alone (considered to be the background noise for the assay); it may therefore be considered that the amounts indicated are the amounts specifically produced in response to the stimulation with the gB protein.

| Groups of mice | γ-IFN | IL5 | TNF-α |
|---|---|---|---|
| gB alone | 2193 | 399 | 61 |
| gB + ethyl DOPC | 56 338 | 416 | 310 |
| gB + ethyl DSPC | 28 756 | 32 | 93 |
| gB + ethyl DSPC + emulsion | 3432 | 4054 | 134 |

All the results produced in this assay show the good adjuvant effect of the phosphoric esters of phosphatidylcholine, which have a large capacity for increasing the Th1-type immune response (increase in IgG2a and in γ-interferon), without, however, inhibiting the Th2-type response already induced by the antigen.

3. Vaccine Compositions Administered Intradermally 3.1. Preparation of the Compositions Powdered 1,2-dioleoyl-sn-glycero-3-ethylphosphocholine (ethyl DOPC) chloride is provided, supplied by the company Avanti® Polar Lipids Inc., 5 mg of which is solubilized in 10 ml of 4:1 (vol/vol) chloroform/methanol. The solution obtained is dried in a glass round-bottomed flask by means of a rotary evaporator so as to leave a lipid film over the walls of the round-bottomed flask. This film is then dried under a strong vacuum in order to remove all traces of residual solvent, and is then taken up in 2.5 ml of water at 60° C. for a final concentration of 2 mg/ml. The resulting liposomal suspension is homogenized by vortexing for 10 minutes, sonication in an ultrasound bath for 5 minutes, and is then extruded by means of a Lipex extruder (Northern Lipids Inc., Vancouver, CA) thermostated at 50° C., in one passage through a 0.8 μm polycarbonate membrane and then one passage through a 0.4 μm polycarbonate membrane and, finally, five passages through a polycarbonate membrane with a porosity of 0.2 μm.

A stock solution of antigen consisting of gB protein is also provided, obtained as described in the preceding example, at a concentration of 160 μg/ml.

The antigen solution is mixed with the suspension of adjuvant at 2 mg/ml in proportions calculated to obtain the experimental vaccines having, per dose of 50 μl, the following compositions:

1) 2 μg of gB,
2) 2 μg of gB and 50 μg of ethyl DOPC
3) 0.2 μg of gB,
4) 0.2 μg of gB and 50 μg of ethyl DOPC.

3.2 Immunization 4 groups of eight 8-week-old OF1 mice are provided.

Each group of mice is given one of the 4 formulations indicated above, intradermally.

The immunizations are performed on D0 and D20.

Blood samples are taken from the retroorbital sinus on D20 before the 2nd immunization in order to assess the primary response and on D35 for the secondary response.

The specific IgG1 and IgG2a titers are determined by means of standardized ELISA assays.

The mice are sacrificed on D35; their spleen is removed and the splenocytes are isolated and stimulated with recombinant gB protein, or not stimulated.

The concentration of cytokines (IL5, γ-IFN and TNF-α) in the supernatants from spleen cells stimulated for 5 days with gB protein, and also in the supernatants from non-stimulated cells, is determined by means of ELISA assays in order to deduce therefrom, by comparison, the specific production of cytokines.

The results obtained with regard to the humoral responses are recapitulated in the table below, in which the IgG titers are expressed in arbitrary ELISA units (log10).

For each group of mice, the value indicated is the mean geometric titer of the values obtained for each of the mice.

| Groups of mice | IgG1 titer at D20 | IgG2a titer at D20 | IgG1 titer at D35 | IgG2a titer at D35 |
|---|---|---|---|---|
| 2 μg gB | 2.095 | 1.097 | 4.478 | 2.829 |
| 2 μg gB + ethyl DOPC | 4.111 | 3.574 | 5.023 | 4.766 |
| 0.2 μg gB | 1.351 | 1.185 | 2.738 | 1.647 |
| 0.2 μg gB + ethyl DOPC | 3.621 | 2.607 | 4.698 | 4.087 |

The results for the cytokines are given in the table below; the values indicated are, for each cytokine, the difference in pg/ml between the mean of the amounts of cytokines measured for the cells restimulated with gB protein, and the mean of the amounts of cytokine measured for the cells cultured in medium alone (considered to be the background noise for the assay); it can therefore be considered that the amounts indicated are the amounts specifically produced in response to the stimulation with the gB protein.

| Groups of mice | γ-IFN | IL5 | TNF-α |
|---|---|---|---|
| 2 μg gB | 3295 | 1891 | 65 |
| 2 μg gB + ethyl DOPC | 49 716 | 1373 | 638 |
| 0.2 μg gB | 2892 | 102 | 135 |
| 0.2 μg gB + ethyl DOPC | 37 877 | 690 | 533 |

In this assay, it is seen that the adjuvant according to the invention is effective when used intradermally, and that it makes it possible both to increase the immune response for the same amount of antigens, or to reduce the amount of antigens present in the injected dose.

Here, the adjuvant effect is visible both with respect to the Th2-type response (IgG1) and also, and even very spectacularly, with respect to the Th1-type response (IgG2a, γ-interferon).

4. Vaccine Compositions Having a SARS Antigen 4.1. Preparation of the Compositions A viral suspension of an inactivated human coronavirus, in this case the SARS (Severe Acute Respiratory Syndrome) virus, obtained by culture on a cell line and then inactivation, is prepared; the suspension used is at a concentration of 7.56 log $CCID_{50}$ before inactivation; it is diluted 1/10 in order to obtain a suspension having a concentration of 6.56 log $CCID_{50}$.

Powdered 1,2-dioleoyl-sn-glycero-3-ethylphosphocholine (ethyl DOPC) chloride is provided, supplied by the company Avanti® Polar Lipids Inc., 30 mg of which is solubilized in 10 ml of 4:1 (vol/vol) chloroform/methanol. The solution obtained is dried in a glass round-bottomed flask by means of a rotary evaporator so as to leave a lipid film over the walls of the round-bottomed flask. This film is then dried under a strong vacuum in order to remove all traces of residual solvent, and is then taken up in 5 ml of water at 60° C. for a final concentration of 6 mg/ml. The resulting liposomal suspension is homogenized by vortexing for 10 minutes, and sonication in an ultrasound bath for 5 minutes, and is then extruded by means of a Lipex extruder (Northern Lipids Inc., Vancouver, CA) thermostated at 50° C., in five passages through a polycarbonate membrane with a porosity of 0.2 μm.

Immunization doses of 200 μl are prepared by effecting the mixtures indicated in the table below:

| Water | Viral suspension at 6.56 log TCID$_{50}$ | Adjuvant | Phosphate buffer | Amount of virus per dose |
|---|---|---|---|---|
| 1.418 ml | 110 μl dil. $^{1}/_{10}$ | — | 472 μl | $10^{4.6}$CCID$_{50}$ |
| 1.151 ml | 110 μl dil. $^{1}/_{10}$ | 267 μl ethyl DOPC | 472 μl | $10^{4.6}$CCID$_{50}$ |
| 1.418 ml | 110 μl dil. 1 | — | 472 μl | $10^{5.6}$CCID$_{50}$ |
| 1.151 ml | 110 μl dil. 1 | 267 μl ethyl DOPC | 472 μl | $10^{5.6}$CCID$_{50}$ |

4.2 Immunization 4 groups of 8 BALB/c mice are provided, and are immunized at 3-week intervals with one of the formulations indicated above; the injections are given subcutaneously; the doses injected are 200 μl each time.

Blood samples are taken 2 weeks after each injection in order to evaluate anti-whole (inactivated) SARS virus antibody responses by ELISA assay, i.e. on D14 for the primary response and on D33 for the secondary response.

The spleen cells are removed on D33.

The SARS-specific cellular response is evaluated by means of an ELISPOT assay of the cells secreting γ-interferon, either ex vivo, or after in vitro stimulation with inactivated whole virus for 7 days. In each case, the spleen cells (ex vivo or restimulated in vitro) are incubated for 16 hours either with inactivated whole virus or with pooled 18-mer peptides, the sequences of which are overlapping (over 10 amino acids) and correspond to various SARS virus antigens.

In addition, the polarization of the T-helper cellular response induced is assessed by means of an ELISA assay of the cytokines secreted by the spleen cells stimulated with the whole inactivated virus or with a pool of peptides.

The results obtained with regard to the humoral response are given in the table below; they are expressed in log10 of arbitrary units of the ELISA assay, and represent the means of the geometric titers for each group of mice.

| Immunizing composition | IgG titer at D14 | IgG titer at D33 |
|---|---|---|
| $10^{4.6}$CCID$_{50}$ | 1 | 1.191 |
| $10^{4.6}$CCID$_{50}$ + ethyl DOPC | 1.246 | 2.424 |
| $10^{5.6}$CCID$_{50}$ | 1.776 | 3.122 |
| $10^{5.6}$CCID$_{50}$ + ethyl DOPC | 2.621 | 4.387 |

These results show that the adjuvant according to the invention makes it possible to increase the humoral response against a viral antigen.

As regards the cellular response, the results obtained in the ELISPOT count carried out on fresh cells (ex vivo) stimulated with whole virus are represented in the table below, which indicates the geometric mean for each group of mice.

| Immunizing composition | Number of spots/$10^6$ spleen cells |
|---|---|
| $10^{4.6}$CCID$_{50}$ | 2 |
| $10^{4.6}$CCID$_{50}$ + ethyl DOPC | 18 |
| $10^{5.6}$CCID$_{50}$ | 17 |
| $10^{5.6}$CCID$_{50}$ + ethyl DOPC | 132 |

As regards the results obtained in response to the peptide pools, the responses vary according to the peptide pools used.

The ELISPOT results obtained after restimulation with inactivated SARS virus also showed that the production of γ-interferon was increased in the presence of ethyl DOPC, in response to some of the peptides used.

These results show that the adjuvant according to the invention makes it possible to increase the CD4+ T-cell response against a viral antigen.

As regards the ELISA assays for the cytokines γ-IFN (Th1 cytokine) and IL-5 (Th2 cytokine), it was noted that, after stimulation with inactivated virus, the production of γ-IFN was considerably increased for the mice which had been given ethyl DOPC in addition to the antigen; on the other hand, the production of IL-5 was not clearly modified.

The results obtained are given in the table below; they are expressed in pg/ml, and represent the geometric means of the groups of mice.

| | Stimulation with the inactivated whole virus | |
|---|---|---|
| Immunizing composition | γ-IFN (pg/ml) | IL-5 (pg/ml) |
| $10^{4.6}$TCID$_{50}$ | 4910 | 2793 |
| $10^{4.6}$TCID$_{50}$ + ethyl DOPC | 9262 | 3037 |
| $10^{5.6}$TCID$_{50}$ | 7223 | 3649 |
| $10^{5.6}$TCID$_{50}$ + ethyl DOPC | 51 453 | 5270 |

These results show that the adjuvant according to the invention makes it possible to increase the Th1-type cellular response.

Thus, all these results show that the adjuvant according to the invention makes it possible to significantly increase both the cellular (Th1) and humoral immune response induced when an antigen consisting of an inactivated virus is administered.

The invention claimed is:

1. A method for immunizing a mammal, the method comprising administering to said mammal at least one vaccine antigen and a phosphoric ester derivative of phosphatidylcholine having the structure:

$$\begin{array}{c} H_2C-O-\overset{O}{\overset{\|}{C}}-R_3 \\ | \\ HC-O-\overset{O}{\overset{\|}{C}}-R_2 \\ | \\ H_2C-O-\overset{O}{\overset{\|}{\underset{OR_1}{P}}}-O-CH_2-CH_2-\overset{CH_3}{\overset{|}{\underset{CH_3}{N^{\oplus}}}}-CH_3 \end{array} \quad (I)$$

wherein,

R$_1$ is a lower alkyl,

R$_2$ and R$_3$ are identical or different, and each is a linear hydrocarbon-based chain having from 13 to 21 carbon atoms.

2. The method according to claim 1 wherein $R_1$ is ethyl.

3. The method according to claim 1 wherein $R_2$ and $R_3$ are chosen from the radicals originating from myristic acid, palmitic acid, stearic acid or oleic acid.

4. The method according to claim 1 wherein $R_2$ and $R_3$ are both identical and represent the oleic acid radical.

5. The method according to claim 2 wherein $R_2$ and $R_3$ are chosen from the radicals originating from myristic acid, palmitic acid, stearic acid or oleic acid.

6. The method according to claim 5 wherein $R_2$ and $R_3$ are both identical and represent the oleic acid radical.

* * * * *